United States Patent [19]
Seth

[11] Patent Number: 5,611,789
[45] Date of Patent: Mar. 18, 1997

[54] DISPOSABLE DIAPER MECHANICAL CLOSURE SYSTEM WITH ADHESIVE DISPOSABILITY

[75] Inventor: Jayshree Seth, Woodbury, Minn.

[73] Assignee: Minnesota Mining and Manufacturing Company, St. Paul, Minn.

[21] Appl. No.: 400,748

[22] Filed: Mar. 8, 1995

[51] Int. Cl.⁶ .................................................. A61F 13/15
[52] U.S. Cl. .......................................... 604/391; 604/389
[58] Field of Search ..................................... 604/365, 367, 604/385.1, 386, 387, 389–391

[56] References Cited

U.S. PATENT DOCUMENTS

| | | |
|---|---|---|
| 3,869,761 | 3/1975 | Schaar . |
| 4,699,622 | 10/1987 | Toussant et al. . |
| 4,869,724 | 9/1989 | Scripps .................................. 604/389 |
| 4,963,140 | 10/1990 | Robertson et al. ..................... 604/389 |
| 5,019,065 | 5/1991 | Scripps .................................. 604/385.1 |
| 5,053,028 | 10/1991 | Zoia et al. ............................. 604/385.1 |
| 5,108,384 | 4/1992 | Goulait .................................. 604/390 |
| 5,176,670 | 1/1993 | Roessler et al. ....................... 604/389 |
| 5,176,671 | 1/1993 | Roessler et al. ....................... 604/391 |

FOREIGN PATENT DOCUMENTS

| | | | |
|---|---|---|---|
| 0321232 | 6/1989 | European Pat. Off. ................ 604/391 |
| 0324578A1 | 7/1989 | European Pat. Off. ........ A41B 13/02 |
| 0563457A1 | 10/1993 | European Pat. Off. ........ A61F 13/56 |
| 0563457 | 10/1993 | European Pat. Off. ................ 604/390 |
| 2087805 | 12/1971 | France ............................. A41B 13/00 |
| 9319713 | 10/1993 | WIPO .................................... 604/389 |
| 9319712 | 10/1993 | WIPO .................................... 604/389 |

OTHER PUBLICATIONS

PCT International Search Report.

*Primary Examiner*—John G. Weiss
*Assistant Examiner*—Kin Yong O
*Attorney, Agent, or Firm*—Gary L. Griswold; Walter N. Kirn; William J. Bond

[57] ABSTRACT

A disposable absorbent article such as a diaper, is provided with a mechanical fastener closure system comprising a hook and loop type mechanical fastener and a pressure-sensitive adhesive fastener. A hook, or loop, element is provided on one face of a first substrate with a pressure-sensitive adhesive tape tab on the opposing face with a free end that is releasably secured to the hook or loop element on the first face. A second substrate is provided with a mating mechanical fastener, to the one on the first face, the tape tab allowing the article to be rolled up for disposal.

8 Claims, 2 Drawing Sheets

DISPOSABLE DIAPER MECHANICAL CLOSURE SYSTEM WITH ADHESIVE DISPOSABILITY

The present invention relates to a mechanical fastener closure system used on a disposable diaper with means to hold the diaper in a folded or rolled condition for disposal.

Closure systems for disposable diapers are conventionally pressure-sensitive adhesive fastening tape tabs that are permanently attached to ears or corners of a diaper at one diaper end and releasably attached to a front panel region of the diaper outer face at a second opposing end of the diaper. The diaper is designed such that the adhesive fastening tape tab can be removed from the frontal region when the diaper is soiled, without tearing the diaper backsheet or destroying the adhesive properties of the diaper fastening tape tab. The user generally then folds or rolls up the diaper and uses the tape tab(s) to keep the diaper from unfolding during disposal. This disposal use of the fastening tape tab is generally not a use that the manufacturer teaches the user (e.g., parent), rather the use of the adhesive fastening tape tab for disposal of the folded diaper is a natural tendency for most users. However as individuals react differently, how the diaper is folded and how the tapes are adhered tends to differs between individuals. Inevitably, however, the tape will be adhered to the backsheet or outer face of the diaper. With conventional diapers, with polyethylene-based film backsheets, conventional diaper fastening tape tabs will generally readily adhere to the backsheet film securely enough to keep the diaper from opening while it is being disposed of.

Recently the use of mechanical closures for diapers has been proposed. The mechanical closure is typically a hook and loop type mechanical fastener. The hook portion of the mechanical fastener generally is placed on the diaper at the location where the pressure-sensitive adhesive fastening tab is typically located. A mating loop patch is then placed on the diaper frontal portion, where a fastening tape tab would typically be releasably attached by the user. The mating loop patch is located on the diaper end opposite the diaper end where the hook is permanently attached.

Generally, when a diaper is folded or rolled up for disposal and the fastening tab is used to keep the diaper folded, the fastening tab is attached to the backsheet at a location other than where the fastening tab attaches for closure. Consequently, with mechanical closures, the mating loop patch is not at a location where it is usable for disposal or the diaper. Therefore, the fastening tab must adhere to another appropriately placed loop patch or some other disposal strategy must be used. For example, as disclosed in U.S. Pat. No. 5,176,671, when used for disposal, a fastening tab free end is conventionally attached to the backsheet at the same diaper end, generally the back end, as that in which the fastening tab is permanently attached. The front end is the end where the mating loop patch is placed to attach to the fastening tab free end for closure, which is generally the front end. Unless this back end location is also supplied with a suitable loop patch, the mechanical fastening tab hook material cannot be used to keep a diaper folded for disposal. However, as discussed above, as different individuals will wish to place the fastening tab at different locations for disposal, a large number of loop patches or a very large loop patch must be used at the back end. To address this problem it is has been proposed in a large number of patent applications to use a separate pressure-sensitive adhesive fastening element for disposability purposes only. This separate pressure-sensitive adhesive fastening element eliminates the need for a separate loop patch at the diaper back end. U.S. Pat. No. 5,053,028 proposes a number of different embodiments where hook fastening elements are located on a terminal end of a tab, which tab, at the opposing end, is permanently attached to the diaper. An exposed or exposable pressure-sensitive adhesive layer is located on this same tab, which can be used for disposability after the diaper is soiled and rolled up for disposal. In certain embodiments, the pressure-sensitive adhesive is exposed during use. In other embodiments, the pressure-sensitive adhesive is protected prior to disposal.

A similar approach is proposed in U.S. Pat. No. 5,019,065 which proposes using an area of exposed adhesive directly on the tape tab, which exposed adhesive allows the mechanical fastener and tape tab to be used in subsequent disposal of the diaper.

U.S. Pat. No. 4,963,140 proposes using a number of different means to allow the diaper to remain folded for disposal, including a pressure-sensitive adhesive on the fastening tab containing the mechanical fastening elements and a separate pressure-sensitive adhesive tab, which is used exclusively for disposal purposes. U.S. Pat. No. 5,176,671, discussed above, also proposes use of a pressure-sensitive adhesive section, for use in disposability, on a fastening tab containing hook elements.

U.S. Pat. No. 5,108,384 proposes a protected pressure-sensitive adhesive on a mechanical fastening tab for disposability. However, a primary pressure-sensitive adhesive is also provided, which is unprotected when the mechanical fastener is used. The protected secondary pressure-sensitive adhesive is used as a reserve system for disposability purposes should the primary pressure-sensitive adhesive become contaminated.

In European Patent Application No. 563457 A1, a mechanical fastener system is disclosed, again with an exposed area of pressure-sensitive adhesive on the fastening tab containing the mechanical fastening elements. In this disclosure, a release tape tab is provided which protects the adhesive prior to the fastening tab being used to close the diaper. This release tab is of a length only sufficient to protect the pressure-sensitive adhesive and not overlap with the mechanical fastening elements.

DETAILED DESCRIPTION OF THE PREFERRED EMBODIMENTS

The closure systems of the invention are used with disposable articles which use at least one mechanical fastener tab patch as the primary closure when the article is being used and which articles are subsequently folded or rolled for disposability purposes and secured with a separate adhesive tab for disposability. Generally, disposable absorbent articles of this type are diapers, adult incontinent products, or feminine hygiene products with an outer layer of a water impermeable thermoplastic film. However other disposable articles that use mechanical fastener tab closures and are rolled up, or the like, for disposal, such as hospital gowns, could use the invention closure system. The invention closure system will be described in reference to a conventional disposable diaper structure.

Figure 1:
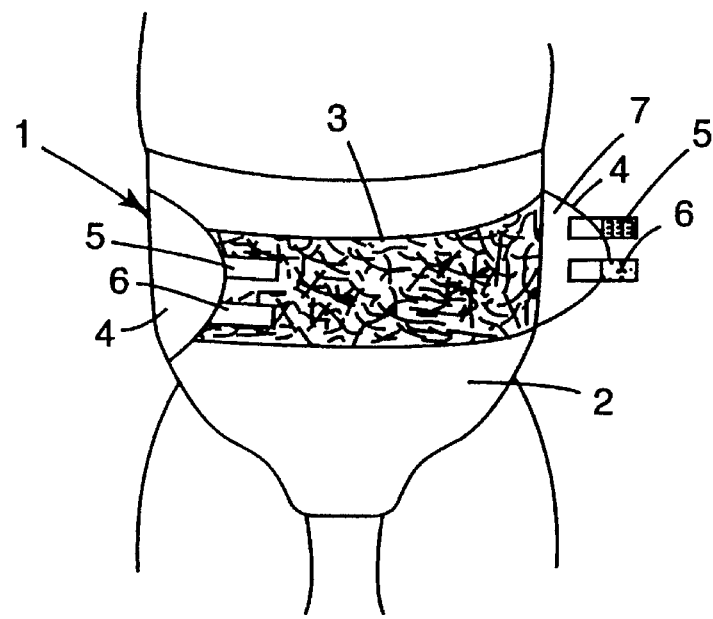
FIG. 1 is a perspective view showing a prior art diaper design with a separate pressure-sensitive adhesive fastening tab for disposability.

Referring to FIG. 1 there is disclosed a conventional diaper 1 with a liquid permeable topsheet 7 and a liquid impermeable backsheet 2, as it would be worn on a baby. On two opposing ears 4 are provided tabs 5, which contain mechanical fastening elements, generally hook or mushroom-type mechanical fastening elements. This structure is disclosed in U.S. Pat. No. 4,869,724 and it uses a separate pressure-sensitive adhesive fastening tab 6 to keep the diaper in a folded form for disposability. Fastening tape tab 6 attaches to the diaper backsheet 2 when it is folded. Backsheet 2 typically is a thin thermoplastic film, generally a thin polyethylene film. The pressure-sensitive adhesive fastening tab 6 used for disposability would typically be folded onto a release tab and exposed only when disposing of the diaper.

Figure 2:
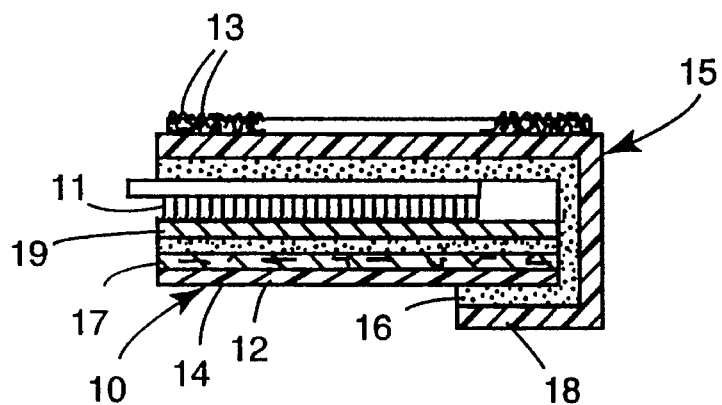
FIG. 2 is a cross-sectional view of a prior art diaper mechanical fastening tab with a separate loop patch on the fastening tab for disposability.

In the FIG. 2 prior art embodiment, there is shown a provision of a separate loop patch on a backface of a mechanical fastener closure tab. This loop patch can be used such that the hooks on the mechanical fastener closure tab attach to the loop patch on the opposite tab when the diaper is rolled up for disposal. The mechanical fastening elements 11 are provided on a backing which is adhered to the fastening tab 15 with a pressure-sensitive adhesive layer 16 provided on a fastening tab backing 18. The pressure-sensitive adhesive layer 16 also permanently attaches the fastening tab 15 to the diaper ear 14, which as shown comprises a diaper backsheet 12 and a diaper topsheet 17. Also provided on the diaper topsheet 17 is release tape tab 19, which comprises a backing layer with a release coating attached to the diaper ear 14 by a pressure-sensitive adhesive layer. The loop patch 13 can be suitably attached to the fastening tab 15 by use of adhesive, heat bonding or the like. This construction is somewhat complicated and difficult to manufacture.

Figure 3:
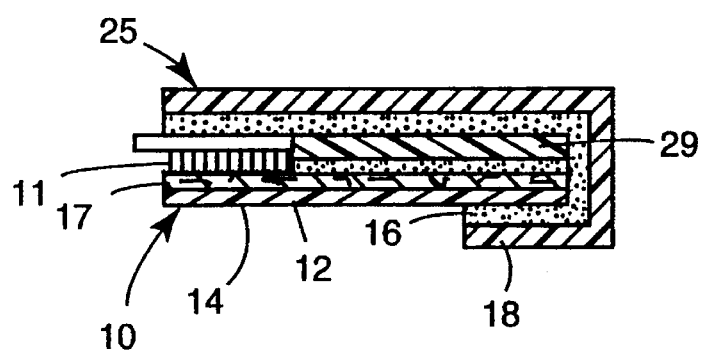
FIG. 3 is another cross-sectional view of a prior art diaper mechanical fastening tab with a pressure-sensitive adhesive region for disposability.

FIG. 3 discloses another prior art arrangement where mechanical fastening elements 11 are located on a fastening tab 25 formed of a backing 18 and a pressure-sensitive adhesive layer 16, similar to that shown in FIG. 2. In this embodiment there is a large area of the pressure-sensitive adhesive layer 16 which is allowed to remain exposed. This exposed adhesive can be used for disposability purposes. The tab 25 is again attached to a corner ear of the diaper 14 formed of a diaper backsheet 12 and topsheet 17. Release tape tab 29 only protects the exposed portion of the pressure-sensitive adhesive layer 16.

Figure 4:
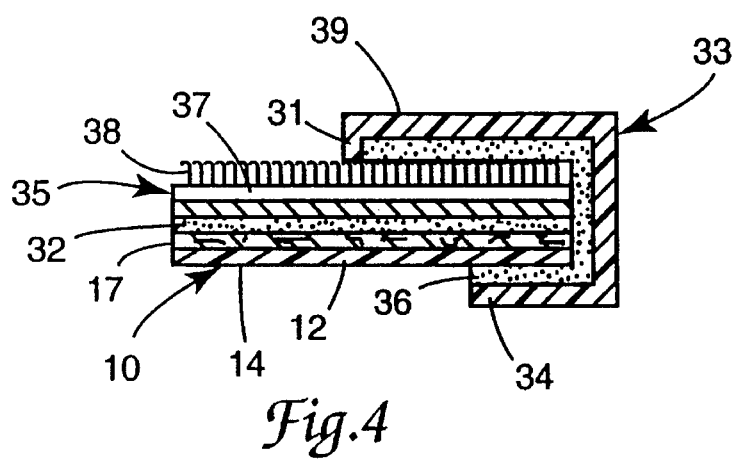
FIG. 4 is a cross-sectional view of the invention closure system with a mechanical fastener tape tab and a separate pressure-sensitive adhesive tape tab provided for disposability.

FIG. 4 shows a preferred embodiment of the invention closure system on a diaper ear or edge region 14. The mechanical fastener 35 is placed on the inner face of the diaper ear or edge region 14, which generally comprises a water permeable topsheet 17 such as a nonwoven web or other known liquid permeable webs. Mechanical fastener 35 is attached, e.g., to the topsheet 17 by use of a suitable attachment such as an adhesive layer 32, which preferably is a pressure-sensitive adhesive suitably formulated to attach to the topsheet material 17 or whatever material forms the inner face of ear or edge region 14. The mechanical fastener 35 comprises a backing 37 with individual projecting hook elements 38 extending out and terminating in a fiber engaging top section. Generally the hook shape would comprise a mushroom-type hook structure, a J-type hook, a T-type hook or other suitable hook shapes with fiber engaging top structures. The fiber engaging top structures most often are overhanging lip(s) projecting from a upstanding stem. The overhanging lip is suitably sized to engage fibers of a mating loop material, which loop material is provided on an opposing end of the diaper. Mechanical fastener 35 is located directly adjacent the outermost edge of ear or edge region 14, however, the fastener 35 could be displaced a small distance from this outermost edge. The mechanical fastener 35 is of a size and shape sufficient to provide a secure attachment to the selected mating loop material. As such the size of the mechanical fastener 35 will depend on the particular hook and loop materials selected. Generally, the mechanical fastener 35 will be a rectangular type of tab for ease of use, manufacturability and cost, however, other shapes are also functional. Suitable selection of commercially available matched mechanical fastener hook materials and loop materials is within the skill of the art.

In the invention closure system a tape tab 33, for disposability, is also provided directly adjacent the outermost edge of the ear or edge region 14. A manufacturers bond end 34 of the tape tab 33 is attached to the outer face of the diaper 10 at the ear or edge region 14, which generally is a water impermeable thermoplastic film or film laminate, e.g., with a nonwoven. The adhesive layer 36 on the tape tab 33 is designed to securely and permanently bond to the outer sheet 12, which outer sheet 12 is provided generally both on the ear or edge region 14 and the main body portion of the diaper 10. User end 39 of the pressure-sensitive adhesive tape tab 33 is removably secured to the mechanical fastener 35 and generally covers less than the entire length of the mechanical fastener 35. As such, the user end 39 of tape tab 33 is generally of the same width or narrower than the mechanical fastener 35 such that no adhesive is in contact with the ear or edge region 14. The mechanical fastening elements 38 on mechanical fastener 35 provide a release surface for the pressure-sensitive adhesive layer 36 due to the low surface area available for contact by the pressure-sensitive adhesive layer. As such, the tape tab 33 can be readily removed from the mechanical fastener 35 without the need for providing a release coating on the outer surface of the mechanical fastener 35. The mechanical fastening elements 38 together act as a mechanical release layer.

Figure 5:
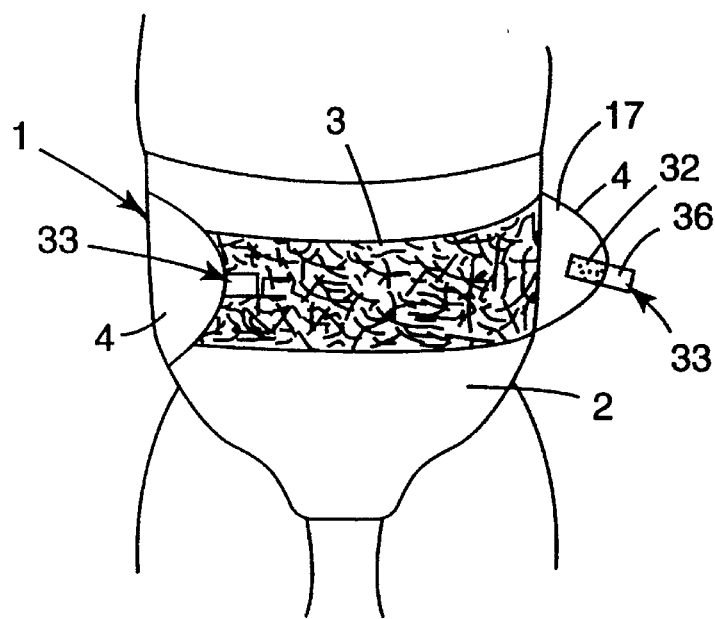
FIG. 5 is a perspective view of a diaper provided with the closure system of FIG. 4.

The pressure-sensitive adhesive layer 36 on the user end 39 is formulated so that it will securely adhere to the outer layer 2 of the main body portion of the diaper 1 such as shown in FIG. 5 when tape tab 33 is removed from the fastening elements 38 on mechanical fastener 35. The user end 39 of tape tab 33 can be removed from the mechanical fastener tab 35 prior to application of the mechanical fastener 35 to the mating loop patch 3 or just immediately prior to disposal of the diaper. In either case user end 39 will provide a convenient means for grasping the attached portion of the diaper ear 4. To facilitate grasping of the user end 39 and fingerlift portion 31 could be provided by leaving a portion of user end 39 uncoated with adhesive, or other known means such as folding over a portion of the distal end of tape tab 33 as shown.

The FIG. 4 embodiment construction eliminates the need for a release tape or tab as shown in the prior art instructions. Further, the invention closure system can be easily implemented by a diaper manufacturer without requiring complex lamination of a mechanical fastener tab portion and tape tab products. Mechanical fastener 35 and the pressure-sensitive adhesive tape tab 33 used for disposability can be provided from separate rolls of stock material and cut into tabs and applied sequentially on a diaper manufacturing line using conventional equipment. The tape tab 33 provides an adhesive tape tab user end 39 which can be used to secure the diaper in a folded or rolled condition for disposal allowing the diaper to be easily thrown away without opening up and releasing any of the contents of the diaper.

The loop patch 3 on the diaper 1 of FIG. 5 can be any suitable material which is engagable with the mechanical fastener 35. Generally, the loop patch is a nonwoven, woven or knitted material provided with open fibrous loop structures allowing suitable mechanical fastening elements 38 to penetrate the fiber structure and engage individual fibers in the loop patch with the fiber engaging top structures. The loop patch can be applied by suitable attachment means including the use of a pressure-sensitive adhesive, sonic welding or the like. A preferred application is as a pressure-sensitive adhesive loop tape where a back portion of the loop patch is provided with a pressure-sensitive adhesive for application to the diaper backsheet 2. Preferably, the loop patch is previously coated or otherwise provided with a film layer 37 on the face attached to the diaper to provide a surface for coating a pressure-sensitive adhesive.

The loop patch can be a unitary structure across the entire width of diaper 1 or a large portion of the entire width of diaper 1 on a front end portion of the backsheet 2. The loop patch can also be provided as separate individual loop patches placed at suitable locations so as to allow for engagement of the mechanical fastener 35 on each ear portion 4. Again, the loop patch can be of any suitable size and or shape, however, preferably it is rectangular for manufacturing and cost considerations.

I claim:

1. A disposable article having a mechanical fastener closure system comprising a disposable article having two opposing substrate portions to be attached, a first substrate portion having a first mechanical fastening element comprising a fibrous loop patch directly and permanently attached to a first face of said first substrate portion, a second mechanical fastening element comprising a male mechanical fastener having a backing, said backing having a first face and a second face with the first face having individual projecting hook elements engagable with the fibers of said fibrous loop patch and said backing second face directly and permanently attached to a first face of a second of said two opposing substrate portions directly adjacent an outermost edge of said second substrate portion, and a pressure-sensitive adhesive tape tab having a first end pressure-sensitive adhesive portion and a second end pressure-sensitive adhesive portion, said tape tab first end portion being releasably secured by said first end pressure-sensitive adhesive to said second mechanical fastening element projecting hook elements and said tape tab second end portion pressure-sensitive adhesive being permanently secured to a second face of said second substrate portion, wherein said first mechanical fastening element is mechanically attachable with said second mechanical fastening element so as to secure said first and second substrate portions in an overlapping relationship and said pressure-sensitive adhesive tape tab first end pressure-sensitive adhesive portion is removable from said second mechanical fastening element so as to secure to a face of said disposable article to keep said disposable article in a rolled or folded condition prior to disposal.

2. The disposable article having a mechanical fastener closure system of claim 1 wherein said disposable article comprises a disposable diaper having a body portion, an outer surface and an inner surface, said loop patch attached to the outer surface of said diaper at a first end region forming said first substrate portion and said male mechanical fastener is attached to said inner surface of said diaper at a second end region forming said second substrate portion and is directly adjacent an outermost side edge region of said diaper.

3. The disposable diaper mechanical fastening system of claim 2 wherein said outer surface comprises a continuous thermoplastic film or film laminate covering the entire diaper and said inside surface comprises a liquid permeable web.

4. The disposable diaper of claim 3 wherein said pressure-sensitive adhesive tape tab second end is permanently attached to said outer surface film or film laminate.

5. The disposable article having a mechanical fastener closure system of claim 1 wherein said pressure-sensitive adhesive tape tab second end portion is of a width less than or equal to the width of said male mechanical fastener and said tape tab first end portion has a length such that at least a portion of an end section of said male mechanical fastener projecting hook elements are not covered by said tape tab first end portion.

6. The disposable article having a mechanical fastener closure system of claim 1 wherein said male mechanical fastener hook elements comprise upstanding stems with a fiber engaging top structure in the form of an overhanging lip element.

7. The disposable article having a mechanical fastener closure system of claim 6 wherein said hook elements have no release coating such that said hook elements provide a mechanical release surface for said tape tab first end portion.

8. The disposable article having a mechanical fastener closure system of claim 1 wherein said male mechanical fastener and said tape tab are rectangular in shape.

\* \* \* \* \*